US008134012B2

(12) United States Patent
Suty-Heinze et al.

(10) Patent No.: US 8,134,012 B2
(45) Date of Patent: Mar. 13, 2012

(54) SYNERGISTIC FUNGICIDAL ACTIVE COMPOUND COMBINATIONS

(75) Inventors: Anne Suty-Heinze, Langenfeld (DE); Burkhard Schütz, Düsseldorf (DE); Gerhard-Johann Feurer, Liederbach (DE); Hans-Ludwig Elbe, Wuppertal (DE)

(73) Assignee: Bayer Cropscience AG, Monheim (DE)

( * ) Notice: Subject to any disclaimer, the term of this patent is extended or adjusted under 35 U.S.C. 154(b) by 1005 days.

(21) Appl. No.: 11/910,516

(22) PCT Filed: Mar. 27, 2006

(86) PCT No.: PCT/EP2006/002779
§ 371 (c)(1),
(2), (4) Date: Feb. 25, 2008

(87) PCT Pub. No.: WO2006/105889
PCT Pub. Date: Oct. 12, 2006

(65) Prior Publication Data
US 2008/0255071 A1 Oct. 16, 2008

(30) Foreign Application Priority Data

Apr. 7, 2005 (DE) .................. 10 2005 015 850

(51) Int. Cl.
C07D 231/00 (2006.01)
C07D 487/00 (2006.01)
C07D 231/56 (2006.01)
(52) U.S. Cl. ............... 548/374.1; 548/358.1; 548/362.5
(58) Field of Classification Search .............. 548/374.1, 548/358.1, 362.5
See application file for complete search history.

(56) References Cited

U.S. PATENT DOCUMENTS

| 5,965,774 A | 10/1999 | Yoshikawa |
| 2008/0139389 A1* | 6/2008 | Kneen et al. .................. 504/100 |
| 2009/0018015 A1* | 1/2009 | Wachendorff-Neumann et al. .............. 504/100 |

FOREIGN PATENT DOCUMENTS

| DE | 2201063 | 7/1973 |
| DE | 2324010 | 1/1975 |
| DE | 19646407 | 5/1998 |
| DE | WO 03/010149 | 2/2003 |
| DE | WO03/010149 | * 2/2003 |
| DE | 103 03 589 | 8/2004 |
| DE | WO 04/067515 | 8/2004 |
| EP | 0 040 345 | 11/1981 |
| EP | 0 382 375 | 8/1990 |
| EP | 0 515 901 | 12/1992 |
| EP | 712396 | 5/1996 |
| EP | 0 824 099 | 2/1998 |
| JP | 2001 072507 A | 3/2001 |
| WO | 97/06171 | 2/1997 |
| WO | 02/38542 A | 5/2002 |
| WO | 2004/005242 A | 1/2004 |

OTHER PUBLICATIONS

Jonathan Gressel, Synergizing Pesticides to Reduce Use Rates, in Pest Control With Enhanced Environmental Safety (ACS Symposium Series vol. 524, 1993).*
International Search Report PCT/EP2004/011403.
International Search Report dated Jan. 30, 2007.
Charles Worthing "A World Compendium" The Pesticide Manual, 9th Edition (1991), pp. 249 and 827.

* cited by examiner

Primary Examiner — Karlheinz R Skowronek
Assistant Examiner — Sean Basquill
(74) Attorney, Agent, or Firm — Baker, Donelson, Bearman, Caldwell & Berkowitz PC

(57) ABSTRACT

The novel active compound combinations comprising a carboxamide of the general formula (I) (group 1)

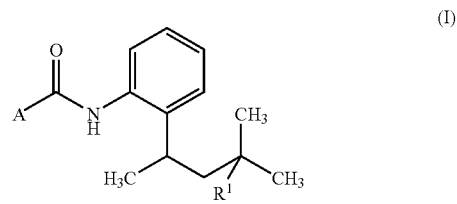

(I)

in which
A, $R^1$ and $R^2$ are as defined in the description,
and the active compound groups (2) and (3) listed in the description have very good fungicidal properties.

15 Claims, No Drawings

SYNERGISTIC FUNGICIDAL ACTIVE COMPOUND COMBINATIONS

CROSS-REFERENCE TO RELATED APPLICATIONS

This application is a §371 national stage application of PCT/EP2006/002779 which claims priority to DE 102005015850, field Apr. 7, 2005.

BACKGROUND OF INVENTION

1. Field of Invention

The present invention relates to novel active compound combinations comprising, firstly, known carboxamides and, secondly, further known fungicidally active compounds, which combinations are highly suitable for controlling unwanted phytopathogenic fungi.

2. Description of Related Art

It is already known that certain carboxamides have fungicidal properties: for example N-[2-(1,3-dimethylbutyl)phenyl]-5-fluoro-1,3-dimethyl-1H-pyrazole-4-carboxamide from WO 03/010149 and 3-(trifluoromethyl)-N-[2-(1,3-dimethylbutyl)phenyl]-5-fluoro-1-methyl-1H-pyrazole-4-carboxamide from DE-A 103 03 589. The activity of these compounds is good; however, at low application rates it is sometimes unsatisfactory. Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th Edition (1991), pages 249 and 827, EP-A 0 382 375 and EP-A 0 515 901). However, the activity of these compounds at low application rates is likewise not always sufficient. Furthermore, it is already known that 1-(3,5-dimethylisoxazole-4-sulphonyl)-2-chloro-6,6-difluoro-[1,3]-dioxolo-[4,5f]benzimidazole has fungicidal properties (cf. WO 97/06171). Finally, it is also known that substituted halopyrimidines have fungicidal properties (cf DE-A1-196 46407, EP-B-712 396).

SUMMARY OF THE INVENTION

This invention now provides novel active compound combinations having very good fungicidal properties and comprising at least one carboxamide of the general formula (I) (group 1)

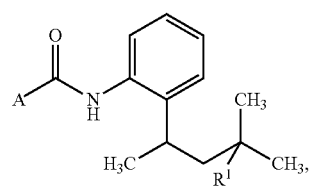

(I)

in which
$R^1$ represents hydrogen, halogen, $C_1$-$C_3$-alkyl or $C_1$-$C_3$-haloalkyl having 1 to 7 fluorine, chorine and/or bromine atoms, A represents one of the radicals A1 to A8 below:

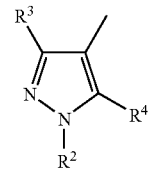

A1

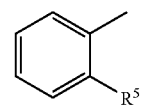

A2

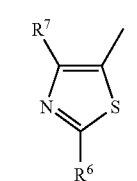

A3

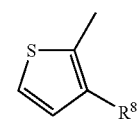

A4

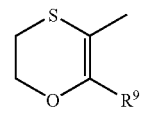

A5

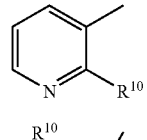

A6

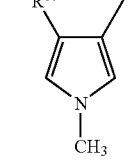

A7

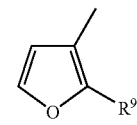

A8

$R^2$ represents $C_1$-$C_3$-alkyl,
$R^3$ represents hydrogen, halogen, $C_1$-$C_3$-alkyl or $C_1$-$C_3$-haloalkyl having 1 to 7 fluorine, chlorine and/or bromine atoms,
$R^4$ represents hydrogen, halogen or $C_1$-$C_3$-alkyl,
$R^5$ represents halogen, $C_1$-$C_3$-alkyl or $C_1$-$C_3$-haloalkyl having 1 to 7 fluorine, chlorine and/or bromine atoms,
$R^6$ represents hydrogen, halogen, $C_1$-$C_3$-alkyl, amino, mono- or di($C_1$-$C_3$-alkyl)amino,
$R^7$ represents hydrogen, halogen, $C_1$-$C_3$-alkyl or $C_1$-$C_3$-haloalkyl having 1 to 7 fluorine, chlorine and/or bromine atoms,
$R^8$ represents halogen, $C_1$-$C_3$-alkyl or $C_1$-$C_3$-haloalkyl having 1 to 7 fluorine, chlorine and/or bromine atoms,
$R^9$ represents halogen, $C_1$-$C_3$-alkyl or $C_1$-$C_3$-haloalkyl having 1 to 7 fluorine, chlorine and/or bromine atoms, $R^{10}$ represents hydrogen, halogen, $C_1$-$C_3$-alkyl or $C_1$-$C_3$-haloalkyl having 1 to 7 fluorine, chlorine and/or bromine atoms, and (2) tolclofos-methyl of the formula

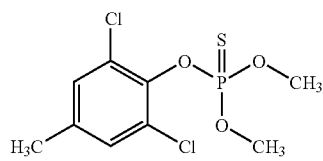

(known from DE-A 25 01 040)

and/or (3) flutolanil of the formula

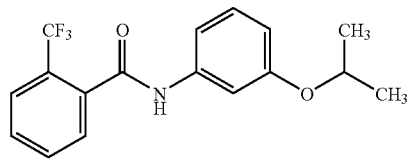

(known from DE-A 27 31 522).

Surprisingly, the fungicidal activity of the active compound combinations according to the invention is considerably higher than the sum of the activities of the individual active compounds. Thus, an unforeseeable true synergistic effect is present, and not just an addition of activities.

DETAILED DESCRIPTION OF A PREFERRED EMBODIMENT

The formula (I) provides a general definition of the compounds of group (1).

Preference is given to carboxamides of the formula (I) in which $R^1$ represents hydrogen, fluorine, chlorine, methyl, ethyl, n-propyl, isopropyl, monofluoromethyl, difluoromethyl, trifluoromethyl, monochloromethyl, dichloromethyl or trichloromethyl, A represents one of the radicals A1 to A5 below:

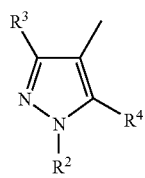

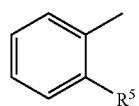

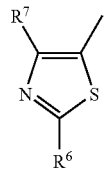

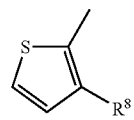

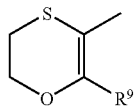

$R^2$ represents methyl, ethyl, n- or isopropyl, $R^3$ represents iodine, methyl, difluoromethyl or trifluoromethyl, $R^4$ represents hydrogen, fluorine, chlorine or methyl, $R^5$ represents chlorine, bromine, iodine, methyl, difluoromethyl or trifluoromethyl, $R^6$ represents hydrogen, chlorine, methyl, amino or dimethylamino, $R^7$ represents methyl, difluoromethyl or trifluoromethyl, $R^8$ represents bromine or methyl, $R^9$ represents methyl or trifluoromethyl.

Particular preference is given to carboxamides of the formula (I) in which $R^1$ represents hydrogen, fluorine, chlorine, methyl, ethyl or trifluoromethyl, A represents one of the radicals A1 or A2 below:

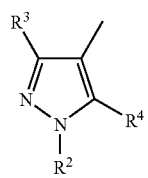

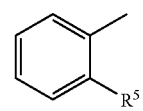

$R^2$ represents methyl or isopropyl, $R^3$ represents methyl, difluoromethyl or trifluoromethyl, $R^4$ represents hydrogen or fluorine, $R^5$ represents iodine, difluoromethyl or trifluoromethyl.

Very particular preference is given to carboxamides of the formula (I) in which $R^1$ represents hydrogen or methyl, A represents one of the radicals A1 or A2 below:

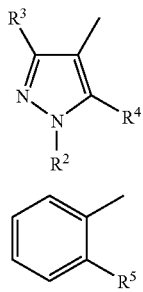

R² represents methyl,
R³ represents methyl,
R⁴ represents fluorine,
R⁵ represents iodine or trifluoromethyl.

Very particular preference is given to using, in mixtures, compounds of the formula (Ia),

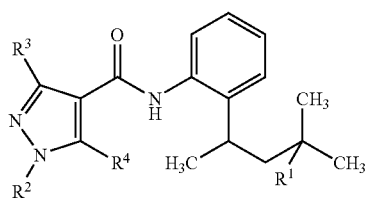

in which $R^1$, $R^2$, $R^3$ and $R^4$ are as defined above.

Very particular preference is given to using, in mixtures, compounds of the formula (Ib)

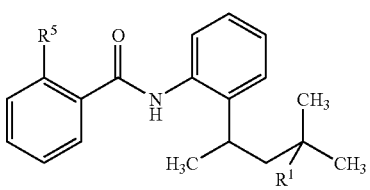

in which $R^1$ and $R^5$ are as defined above.

The formula (I) embraces in particular the following preferred mixing partners of group (1):

(1-1) N-[2-(1,3-dimethylbutyl)phenyl]-1,3-dimethyl-1H-pyrazole-4-carboxamide
(1-2) N-[2-(1,3-dimethylbutyl)phenyl]-5-fluoro-1,3-dimethyl-1H-pyrazole-4-carboxamide (known from WO 03/010149)
(1-3) N-[2-(1,3-dimethylbutyl)phenyl]-5-chloro-1,3-dimethyl-1H-pyrazole-4-carboxamide (known from JP-A 10-251240)
(1-4) 3-(difluoromethyl)-N-[2-(1,3-dimethylbutyl)phenyl]-1-methyl-1H-pyrazole-4-carboxamide
(1-5) 3-(trifluoromethyl)-N-[2-(1,3-dimethylbutyl)phenyl]-5-fluoro-1-methyl-1H-pyrazole-4-carboxamide (known from DE-A 103 03 589)
(1-6) 3-(trifluoromethyl)-N-[2-(1,3-dimethylbutyl)phenyl]-5-chloro-1-methyl-1H-pyrazole-4-carboxamide (known from JP-A 10-251240)
(1-7) 1,3-dimethyl-N-[2-(1,3,3-trimethylbutyl)phenyl]-1H-pyrazole-4-carboxamide (known from JP-A 10-251240)
(1-8) 5-fluoro-1,3-dimethyl-N-[2-(1,3,3-trimethylbutyl)phenyl]-1H-pyrazole-4-carboxamide (known from WO 03/010149)
(1-9) 3-(difluoromethyl)-1-methyl-N-[2-(1,3,3-trimethylbutyl)phenyl]-1H-pyrazole-4-carboxamide
(1-10) 3-(trifluoromethyl)-1-methyl-N-[2-(1,3,3-trimethylbutyl)phenyl]-1H-pyrazole-4-carboxamide
(1-11) 3-(trifluoromethyl)-5-fluoro-1-methyl-N-[2-(1,3,3-trimethylbutyl)phenyl]-1H-pyrazole-4-carboxamide (known from DE-A 103 03 589)
(1-12) 3-(trifluoromethyl)-5-chloro-1-methyl-N-[2-(1,3,3-trimethylbutyl)phenyl]-1H-pyrazole-4-carboxamide (known from JP-A 10-251240)
(1-13) N-[2-(1,3-dimethylbutyl)phenyl]-2-iodobenzamide (known from DE-A 102 29 595)
(1-14) 2-iodo-N-[2-(1,3,3-trimethylbutyl)phenyl]benzamide (known from DE-A 102 29 595)
(1-15) N-[2-(1,3-dimethylbutyl)phenyl]-2-(trifluoromethyl)benzamide (known from DE-A 102 29 595)
(1-16) 2-(trifluoromethyl)-N-[2-(1,3,3-trimethylbutyl)phenyl]benzamide (known from DE-A 102 29 595)

Emphasis is given to active compound combinations according to the invention in which, in addition to the carboxamide (1-8) 5-fluoro-1,3-dimethyl-N-[2-(1,3,3-trimethylbutyl)phenyl]-1H-pyrazole-4-carboxamide (group 1) comprise one or more, preferably one, mixing partner of groups (2) and (3).

Emphasis is given to active compound combinations according to the invention in which, in addition to the carboxamide (1-2) N-[2-(1,3-dimethylbutyl)phenyl]-5-fluoro-1,3-dimethyl-1H-pyrazole-4-carboxamide (group 1) comprise one or more, preferably one, mixing partner of groups (2) and (3).

Emphasis is given to active compound combinations according to the invention in which, in addition to the carboxamide (1-15) N-[2-(1,3-dimethylbutyl)phenyl]-2-(trifluoromethyl)benzamide (group 1) comprise one or more, preferably one, mixing partner of groups (2) and (3).

Emphasis is given to active compound combinations according to the invention in which, in addition to the carboxamide (1-13) N-[2-(1,3-dimethylbutyl)phenyl]-2-iodobenzamide (group 1) comprise one or more, preferably one, mixing partner of groups (2) and (3).

What is described below are preferred active compound combinations comprising two groups of active compounds and in each case at least one carboxamide of the formula (I) (group 1) and at least one active compound of the stated group (2) and (3). These combinations are the active compound combinations A and B.

From among the preferred active compound combinations A and B, emphasis is given to those comprising a carboxamide of the formula (I) (group 1)

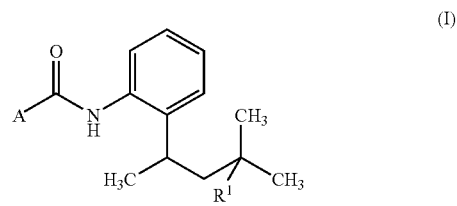

in which $R^1$ and A are as defined above.

Particular preference is given to active compound combinations A and B comprising a carboxamide of the formula (I) (group 1)

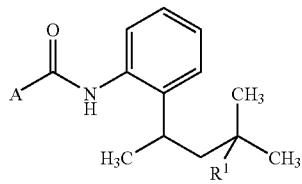

in which
R¹ represents hydrogen, fluorine, chlorine, methyl, ethyl or trifluoromethyl,
A represents one of the radicals A1 or A2 below:

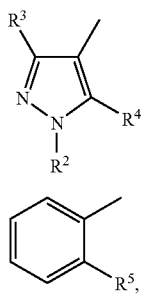

R² represents methyl,
R³ represents methyl, difluoromethyl or trifluoromethyl,
R⁴ represents hydrogen or fluorine,
R⁵ represents iodine or trifluoromethyl.

Very particular preference is given to active compound combinations A and B in which the carboxamide of the formula (I) (group 1) is selected from the list below:
(1-1)  N-[2-(1,3-dimethylbutyl)phenyl]-1,3-dimethyl-1H-pyrazole-4-carboxamide
(1-2)  N-[2-(1,3-dimethylbutyl)phenyl]-5-fluoro-1,3-dimethyl-1H-pyrazole-4-carboxamide
(1-3)  N-[2-(1,3-dimethylbutyl)phenyl]-5-chloro-1,3-dimethyl-1H-pyrazole-4-carboxamide
(1-4)  3-(difluoromethyl)-N-[2-(1,3-dimethylbutyl)phenyl]-1-methyl-1H-pyrazole-4-carboxamide
(1-5)  3-(trifluoromethyl)-N-[2-(1,3-dimethylbutyl)phenyl]-5-fluoro-1-methyl-1H-pyrazole-4-carboxamide
(1-6)  3-(trifluoromethyl)-N-[2-(1,3-dimethylbutyl)phenyl]-5-chloro-1-methyl-1H-pyrazole-4-carboxamide
(1-7)  1,3-dimethyl-N-[2-(1,3,3-trimethylbutyl)phenyl]-1H-pyrazole-4-carboxamide
(1-8)  5-fluoro-1,3-dimethyl-N-[2-(1,3,3-trimethylbutyl)phenyl]-1H-pyrazole-4-carboxamide
(1-9)  3-(difluoromethyl)-1-methyl-N-[2-(1,3,3-trimethylbutyl)phenyl]-1H-pyrazole-4-carboxamide
(1-10)  3-(trifluoromethyl)-1-methyl-N-[2-(1,3,3-trimethylbutyl)phenyl]-1H-pyrazole-4-carboxamide
(1-11)  3-(trifluoromethyl)-5-fluoro-1-methyl-N-[2-(1,3,3-trimethylbutyl)phenyl]-1H-pyrazole-4-carboxamide
(1-12)  3-(trifluoromethyl)-5-chloro-1-methyl-N-[2-(1,3,3-trimethylbutyl)phenyl]-1H-pyrazole-4-carboxamide
(1-13) N-[2-(1,3-dimethylbutyl)phenyl]-2-iodobenzamide
(1-14) 2-iodo-N-[2-(1,3,3-trimethylbutyl)phenyl]benzamide
(1-15) N-[2-(1,3-dimethylbutyl)phenyl]-2-(trifluoromethyl)benzamide
(1-16) 2-(trifluoromethyl)-N-[2-(1,3,3-trimethylbutyl)phenyl]benzamide Especially preferred are active compound combinations A and B in which the carboxamide of the formula (I) (group 1) is selected from the list below:
(1-2)  N-[2-(1,3-dimethylbutyl)phenyl]-5-fluoro-1,3-dimethyl-1H-pyrazole-4-carboxamide
(1-8)  5-fluoro-1,3-dimethyl-N-[2-(1,3,3-trimethylbutyl)phenyl]-1H-pyrazole-4-carboxamide
(1-10)  3-(trifluoromethyl)-1-methyl-N-[2-(1,3,3-trimethylbutyl)phenyl]-1H-pyrazole-4-carboxamide
(1-13) N-[2-(1,3-dimethylbutyl)phenyl]-2-iodobenzamide
(1-14) 2-iodo-N-[2-(1,3,3-trimethylbutyl)phenyl]benzamide
(1-15) N-[2-(1,3-dimethylbutyl)phenyl]-2-(trifluoromethyl)benzamide
(1-16) 2-(trifluoromethyl)-N-[2-(1,3,3-trimethylbutyl)phenyl]benzamide In addition to a carboxamide of the formula (I) (group 1), the active compound combinations A also comprise
(2) tolclofos-methyl of the formula

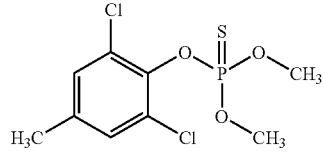

Emphasis is given to the active compound combinations A listed in Table 1 below:

TABLE 1

Active compound combinations A

| No. | Carboxamide of the formula (I) | Mixing partner |
|---|---|---|
| A-1 | (1-2) N-[2-(1,3-dimethylbutyl)phenyl]-5-fluoro-1,3-dimethyl-1H-pyrazole-4-carboxamide | (2) tolclofos-methyl |
| A-2 | (1-8) 5-fluoro-1,3-dimethyl-N-[2-(1,3,3-trimethylbutyl)phenyl]-1H-pyrazole-4-carboxamide | (2) tolclofos-methyl |
| A-3 | (1-10) 3-(trifluoromethyl)-1-methyl-N-[2-(1,3,3-trimethylbutyl)phenyl]-1H-pyrazole-4-carboxamide | (2) tolclofos-methyl |
| A-4 | (1-13) N-[2-(1,3-dimethylbutyl)phenyl]-2-iodobenzamide | (2) tolclofos-methyl |
| A-5 | (1-14) 2-iodo-N-[2-(1,3,3-trimethylbutyl)phenyl]benzamide | (2) tolclofos-methyl |
| A-6 | (1-15) N-[2-(1,3-dimethylbutyl)phenyl]-2-(trifluoromethyl)benzamide | (2) tolclofos-methyl |
| A-7 | (1-16) 2-(trifluoromethyl)-N-[2-(1,3,3-trimethylbutyl)phenyl]benzamide | (2) tolclofos-methyl |

In addition to a carboxamide of the formula (I) (group 1), the active compound combinations B also comprise (3) flutolanil of the formula

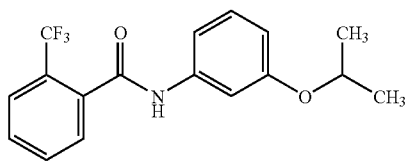

Emphasis is given to the active compound combinations B listed in Table 2 below:

TABLE 2

Active compound combinations B

| No. | Carboxamide of the formula (I) | Mixing partner |
|---|---|---|
| B-1 | (1-2) N-[2-(1,3-dimethylbutyl)phenyl]-5-fluoro-1,3-dimethyl-1H-pyrazole-4-carboxamide | (3) flutolanil |
| B-2 | (1-8) 5-fluoro-1,3-dimethyl-N-[2-(1,3,3-trimethylbutyl)phenyl]-1H-pyrazole-4-carboxamide | (3) flutolanil |
| B-3 | (1-10) 3-(trifluoromethyl)-1-methyl-N-[2-(1,3,3-trimethylbutyl)phenyl]-1H-pyrazole-4-carboxamide | (3) flutolanil |
| B-4 | (1-13) N-[2-(1,3-dimethylbutyl)phenyl]-2-iodobenzamide | (3) flutolanil |
| B-5 | (1-14) 2-iodo-N-[2-(1,3,3-trimethylbutyl)phenyl]benzamide | (3) flutolanil |
| B-6 | (1-15) N-[2-(1,3-dimethylbutyl)phenyl]-2-(trifluoromethyl)benzamide | (3) flutolanil |
| B-7 | (1-16) 2-(trifluoromethyl)-N-[2-(1,3,3-trimethylbutyl)phenyl]benzamide | (3) flutolanil |

In addition to an active compound of the formula (I), the active compound combinations according to the invention comprise at least one active compound from among the compounds of groups (2) and (3). In addition, they may also comprise further fungicidally active added components.

The synergistic effect is particularly pronounced if the active compounds in the active compound combinations according to the invention are present in certain weight ratios. However, the weight ratios of the active compounds in the active compound combinations can be varied within a relatively wide range. In general, the combinations according to the invention comprise active compounds of the formula (I) and a mixing partner from one of the groups (2) and (3) in the mixing ratios given in an exemplary manner in Table 3 below.

The mixing ratios are based on weight ratios. The ratio is to be understood as meaning active compound of the formula (I):mixing partner.

TABLE 3

Mixing ratios

| Mixing partner | preferred mixing ratio | particularly preferred mixing ratio |
|---|---|---|
| (2) tolclofos-methyl | 50:1 to 1:50 | 10:1 to 1:20 |
| (3) flutolanil | 50:1 to 1:50 | 20:1 to 1:20 |

In each case, the mixing ratio is to be chosen such that a synergistic mixture is obtained. The mixing ratios of the compound of the formula (I) and a compound from one of groups (2) and (3) may also vary between the individual compounds of a group.

The active compound combinations according to the invention have a strong microbicidal action and can be used for controlling unwanted microorganisms, such as fungi and bacteria, in crop protection and in the protection of materials.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Diseases caused by powdery mildew pathogens, such as, for example,

Blumeria species, such as, for example, Blumeria graminis;
Podosphaera species, such as, for example, Podosphaera leucotricha;
Sphaerotheca species, such as, for example, Sphaerotheca fuliginea;
Uncinula species, such as, for example, Uncinula necator;

Diseases caused by rust disease pathogens, such as, for example,

Gymnosporangium species, such as, for example, Gymnosporangium sabinae
Hemileia species, such as, for example, Hemileia vastatrix;
Phakopsora species, such as, for example, Phakopsora pachyrhizi and Phakopsora meibomiae;
Puccinia species, such as, for example, Puccinia recondita;
Uromyces species, such as, for example, Uromyces appendiculatus;

Diseases caused by pathogens from the group of the Oomycetes, such as, for example, Bremia species, such as, for example, Bremia lactucae;
Peronospora species, such as, for example, Peronospora pisi or P. brassicae;
Phytophthora species, such as, for example Phytophthora infestans;
Plasmopara species, such as, for example, Plasmopara viticola;
Pseudoperonospora species, such as, for example, Pseudoperonospora humuli or Pseudoperonospora cubensis;
Pythium species, such as, for example, Pythium ultimum;

Leaf blotch diseases and leaf wilt diseases caused, for example, by

Alternaria species, such as, for example, Alternaria solani;
Cercospora species, such as, for example, Cercospora beticola;
Cladiosporium species, such as, for example, Cladiosporium cucumerinum;
Cochliobolus species, such as, for example, Cochliobolus sativus (conidia form: Drechslera, Syn: Helminthosporium);
Colletotrichum species, such as, for example, Colletotrichum lindemuthanium;

*Cycloconium* species, such as, for example, *Cycloconium oleaginum;*
*Diaporthe* species, such as, for example, *Diaporthe citri;*
*Elsinoe* species, such as, for example, *Elsinoe fawcettii;*
*Gloeosporium* species, such as, for example, *Gloeosporium laeticolor;*
*Glomerella* species, such as, for example, *Glomerella cingulata;*
*Guignardia* species, such as, for example, *Guignardia bidwelli;*
*Leptosphaeria* species, such as, for example, *Leptosphaeria maculans;*
*Magnaporthe* species, such as, for example, *Magnaporthe grisea;*
*Mycosphaerella* species, such as, for example, *Mycosphaerelle graminicola;*
*Phaeosphaeria* species, such as, for example, *Phaeosphaeria nodorum;*
*Pyrenophora* species, such as, for example, *Pyrenophora teres;*
*Ramularia* species, such as, for example, *Ramularia collocygni;*
*Rhynchosporium* species, such as, for example, *Rhynchosporium secalis;*
*Septoria* species, such as, for example, *Septoria apii;*
*Typhula* species, such as, for example, *Typhula incamata;*
*Venturia* species, such as, for example, *Venturia inaequalis;*
Root and stem diseases caused, for example, by
*Corticium* species, such as, for example, *Corticium graminearum;*
*Fusarium* species, such as, for example, *Fusarium oxysporum;*
*Gaeumannomyces* species, such as, for example, *Gaeumannomyces graminis;*
*Rhizoctonia* species, such as, for example *Rhizoctonia solani;*
*Tapesia* species, such as, for example, *Tapesia acuformis;*
*Thielaviopsis* species, such as, for example, *Thielaviopsis basicola;*
Ear and panicle diseases (including maize cobs) caused, for example, by
*Alternaria* species, such as, for example, *Alternaria* spp.;
*Aspergillus* species, such as, for example, *Aspergillus flavus;*
*Cladosporium* species, such as, for example, *Cladosporium* spp. such as *Cladosporium cladosporioides;*
*Claviceps* species, such as, for example, *Claviceps purpurea;*
*Fusarium* species, such as, for example, *Fusarium culmorum;*
*Gibberella* species, such as, for example, *Gibberella zeae;*
*Monographella* species, such as, for example, *Monographella nivalis;*
Diseases caused by smut fungi, such as, for example,
*Sphacelotheca* species, such as, for example, *Sphacelotheca reiliana;*
*Tilletia* species, such as, for example, *Tilletia caries;*
*Urocystis* species, such as, for example, *Urocystis occulta;*
*Ustilago* species, such as, for example, *Ustilago nuda;*
Fruit rot caused, for example, by
*Aspergillus* species, such as, for example, *Aspergillus flavus;*
*Botrytis* species, such as, for example, *Botrytis cinerea;*
*Penicillium* species, such as, for example, *Penicillium expansum* and *Penicillium purpurogenum;*
*Sclerotinia* species, such as, for example, *Sclerotinia sclerotiorum;*
*Verticilium* species, such as, for example, *Verticilium alboatrum;*
Seed- and soil-borne rot and wilt diseases, and also diseases of seedlings, caused, for example, by
*Fusarium* species, such as, for example, *Fusarium culmorum;*
*Phytophthora* species, such as, for example, *Phytophthora cactorum;*
*Pythium* species, such as, for example, *Pythium ultimum;*
*Rhizoctonia* species, such as, for example, *Rhizoctonia solani;*
*Sclerotium* species, such as, for example, *Sclerotium rolfsii;*
Cancerous diseases, galls and witches' broom caused, for example, by
*Nectria* species, such as, for example, *Nectria galligena;*
Wilt diseases caused, for example, by
*Monilinia* species, such as, for example, *Monilinia laxa;*
Deformations of leaves, flowers and fruits caused, for example, by
*Taphrina* species, such as, for example, *Taphrina deformans;*
Degenerative diseases of woody plants caused, for example, by
*Esca* species, such as, for example, *Phaemoniella clamydospora;*
Diseases of flowers and seeds caused, for example, by
*Botrytis* species, such as, for example, *Botrytis cinerea;*
Diseases of plant tubers caused, for example, by
*Rhizoctonia* species, such as, for example, *Rhizoctonia solani;*
*Helminthosporium* species, such as, for example, *Helminthosporium solani;*
Diseases caused by bacteriopathogens, such as, for example,
*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora.*

Preference is given to controlling the following diseases of soya beans:

fungal diseases on leaves, stems, pods and seeds caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infimdibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base caused, for example, by
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ulti-*

*mum*), *rhizoctonia* root rot, stem decay, and damping-off (*Rhizoctonia solani*), *sclerotinia* stem decay (*Sclerotinia sclerotiorum*), *sclerotinia* Southern blight (*Sclerotinia rolfsii*), *thielaviopsis* root rot (*Thielaviopsis basicola*).

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fingi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seed of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least considerably reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruit. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, better developed root systems, higher resistance of the plant species and plant cultivars, increased growth of the shoots, higher plant vitality, increased tolerance to high or low temperatures, increased tolerance to drought or to water or soil salt content, increased flowering performance, easier harvesting, accelerated maturation, higher harvest yields, bigger fruit, higher plant heights, greener leaves, earlier flowering, better quality and/or a higher nutritional value of the harvested products, higher sugar concentration in the fruits, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defense of the plants against insects, by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Starlink® (eg maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seed, and ULV cold and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylform de and dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latexes, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a customary manner adapted to the use forms.

The formulations for controlling unwanted phytopathogenic fungi generally comprise between 0.1 and 95% by weight of active compounds, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting etc.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in the fungicides is always present when the fungicidal action of the active compound combinations exceeds the total of the action of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If
X is the efficacy when employing active compound A at an application rate of m g/ha,
Y is the efficacy when employing active compound B at an application rate of n g/ha and
E is the efficacy when employing active compounds A and B at application rates of m and n g/ha,
then $$E = X + Y - \frac{X \times Y}{100}$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

USE EXAMPLES

Example A

*Pyricularia oryzae* Test (In Vitro)/Microtitre Plates

The micro test is carried out in microtitre plates using potato dextrose broth (PDB) as liquid test medium. The active compounds are used as technical-grade a.i., dissolved in acetone, or as a commercial formulation. For inoculation, a spore suspension of *Pyricularia oryzae* is used. After 4 days of incubation in the dark and with shaking (10 Hz), the transparency of each filled cavity of the microtitre plates is determined with the aid of a spectrophotometer. 0% means an efficacy which corresponds to the growth in the controls, whereas an efficacy of 100% means that no fungal growth is observed.

The table below clearly shows that the activity found for the active compound combination according to the invention is greater than the one which had been calculated, i.e. that a synergistic effect is present.

TABLE A

Pyricularia oryzae test (in vitro)/microtitre plates

| Active compounds | Active compound concentration in ppm | Efficacy in % found* | calc.** |
|---|---|---|---|
| (1-2) N-[2-(1,3-dimethylbutyl)phenyl]-5-fluoro-1,3-dimethyl-1H-pyrazole-4-carboxamide | 0.03 | 20 | |
| (2) tolclofos-methyl | 0.03 | 13 | |
| (1-2) N-[2-(1,3-dimethylbutyl)phenyl]-5-fluoro-1,3-dimethyl-1H-pyrazole-4-carboxamide + (2) tolclofos-methyl (1:1) | 0.03 + 0.03 | 55 | 30 |

*found = activity found
**calc. = activity calculated using Colby's formula

Example B

Alternaria mali Test (In Vitro)/Microtitre Plates

The micro test is carried out in microtitre plates using potato dextrose broth (PDB) as liquid test medium. The active compounds are used as technical-grade a.i., dissolved in acetone, or as a commercial formulation. For inoculation, a spore suspension of Alternaria mali is used. After 3 days of incubation in the dark and with shaking (10 Hz), the transparency of each filled cavity of the microtitre plates is determined with the aid of a spectrophotometer. 0% means an efficacy which corresponds to the growth in the controls, whereas an efficacy of 100% means that no fungal growth is observed.

The table below clearly shows that the activity found for the active compound combination according to the invention is greater than the one which had been calculated, i.e. that a synergistic effect is present.

TABLE B

Alternaria mali test (in vitro)/microtitre plates

| Active compounds | Active compound concentration in ppm | Efficacy in % found* | calc.** |
|---|---|---|---|
| (1-2) N-[2-(1,3-dimethylbutyl)phenyl]-5-fluoro-1,3-dimethyl-1H-pyrazole-4-carboxamide | 1 | 83 | |
| (3) flutolanil | 1 | 12 | |
| (1-2) N-[2-(1,3-dimethylbutyl)phenyl]-5-fluoro-1,3-dimethyl-1H-pyrazole-4-carboxamide + (3) flutolanil (1:1) | 1 + 1 | 96 | 85 |

*found = activity found
**calc. = activity calculated using Colby's formula

The invention claimed is:

1. A synergistic fungicidal active compound combination comprising:
    (1) N-[2-(1,3-dimethylbutyl)phenyl]-5-fluoro-1,3-dimethyl-1H-pyrazole-4-carboxamide and
    (2) tolclofos-methyl of the formula

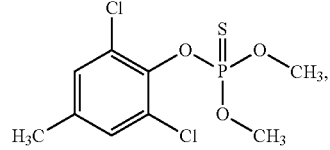

and/or
    (3) flutolanil of the formula;
    wherein a combination comprising N-[2-(1,3-dimethylbutyl)phenyl]-5-fluoro-1,3-dimethyl-1H-pyrazole-4-carboxamide and tolclofos-methyl is in a ratio of 10:1 to 1:20.

2. An active compound combination according to claim 1 comprising a carboxamide comprising N-[2-(1,3-dimethylbutyl)phenyl]-5-fluoro-1,3-dimethyl-1H-pyrazole-4-carboxamide, tolclofos-methyl, and flutolanil.

3. A method for controlling unwanted phytopathogenic fungi comprising utilizing an active compound combination according to claim 1.

4. A method for treating seed comprising applying an active compound combination according to claim 1 to said seed.

5. A method for treating a transgenic plant comprising applying an active compound combination according to claim 1 to said plant.

6. A method for treating seed of a transgenic plant comprising applying an active compound combination according to claim 1 to said seed.

7. Seed treated with an active compound combination according to claim 1.

8. A method for controlling unwanted phytopathogenic fungi, comprising applying an active compound combination according to claim 1 to the unwanted phytopathogenic fungi and/or habitat and/or seed thereof.

9. A process for preparing fungicidal compositions, comprising mixing an active compound combination according to claim 1 with extenders and/or surfactants.

10. A method for controlling unwanted phytopathogenic fungi, comprising applying an active compound combination according to claim 2 to the unwanted phytopathogenic fungi and/or habitat and/or seed thereof.

11. A method for treating seed comprising applying an active compound combination according to claim 2 to said seed.

12. An active compound combination according to claim 1 comprising N-[2-(1,3-dimethylbutyl)phenyl]-5-fluoro-1,3-dimethyl-1H-pyrazole-4-carboxamide and tolclofos-methyl in a ratio of 1:1.

13. The method for treating seed according to claim 4, wherein the seed is a potato seed.

14. The method for treating seed of a transgenic plant according to claim 6, wherein the seed is of a transgenic potato plant.

15. Seed according to claim 7, wherein the seed is a potato seed.

* * * * *